United States Patent
Fleischer et al.

(10) Patent No.: US 8,683,845 B2
(45) Date of Patent: Apr. 1, 2014

(54) CARBON DIOXIDE SENSOR AND ASSOCIATED METHOD FOR GENERATING A GAS MEASUREMENT VALUE

(75) Inventors: Maximilian Fleischer, Hoehenkirchen (DE); Roland Pohle, Herdweg (DE); Stefan Stegmeier, Munich (DE)

(73) Assignee: Siemens Aktiengesellschaft, Munich (DE)

(*) Notice: Subject to any disclaimer, the term of this patent is extended or adjusted under 35 U.S.C. 154(b) by 528 days.

(21) Appl. No.: 12/926,867

(22) Filed: Dec. 14, 2010

(65) Prior Publication Data

US 2011/0146382 A1 Jun. 23, 2011

(30) Foreign Application Priority Data

Dec. 14, 2009 (DE) .................. 10 2009 058 072

(51) Int. Cl.
*G01N 27/00* (2006.01)

(52) U.S. Cl.
USPC .......................... 73/23.21; 73/31.05

(58) Field of Classification Search
USPC .............................. 73/23.21, 31.05
See application file for complete search history.

(56) References Cited

U.S. PATENT DOCUMENTS

| | | | | |
|---|---|---|---|---|
| 5,261,596 | A * | 11/1993 | Tachibana et al. | 236/49.3 |
| 5,418,131 | A * | 5/1995 | Butts | 435/3 |
| 6,241,873 | B1 * | 6/2001 | Namba et al. | 205/784 |
| 6,843,100 | B2 * | 1/2005 | Bair et al. | 73/23.2 |
| 7,946,153 | B2 | 5/2011 | Fleischer et al. | |
| 2005/0028588 | A1 | 2/2005 | Mitter et al. | |
| 2008/0016949 | A1 * | 1/2008 | Fleischer et al. | 73/31.06 |
| 2010/0282245 | A1 * | 11/2010 | Star et al. | 128/200.14 |

FOREIGN PATENT DOCUMENTS

| | | | |
|---|---|---|---|
| CN | 1973201 | 5/2007 | |
| DE | 10 2009 058 072 | 12/2009 | |
| EP | 1 176 418 A2 | 1/2002 | |
| JP | 61-260151 | 11/1986 | |
| JP | 07260726 A * | 10/1995 | G01N 27/12 |
| JP | 8-136490 | 5/1996 | |
| JP | 10-96703 | 4/1998 | |
| JP | 2005-55431 | 3/2005 | |
| JP | 2007-533988 | 11/2007 | |
| WO | WO 2005/103668 A1 | 11/2005 | |

OTHER PUBLICATIONS

Stegmeier, S.; Fleischer, M.; Tawil, A.; Hauptmann, P., "Optimization of the work function response of CO2-sensing Polysiloxane layers by modification of the polymerization," Sensors, 2009 IEEE, pp. 1742-1746, Oct. 25-28, 2009.*

M. Fleischer, B. Ostrick, R. Pohle, E. Simon, H. Meixner, C. Bilger, F. Daeche, "Low-power gas sensors based on work-function measurement in low-cost hybrid flip-chip technology," Sens. Actuators B Chem. 80 (2001) 169-173.*

(Continued)

*Primary Examiner* — Lisa Caputo
*Assistant Examiner* — Punam Roy
(74) *Attorney, Agent, or Firm* — Staas & Halsey LLP

(57) ABSTRACT

A gas sensor detects carbon dioxide, for example for use in air-conditioning systems. The gas sensor is based on a field effect transistor construction. It has a polymer-based material sensitive to carbon dioxide as gas-sensitive layer. The material has a cross-sensitivity with respect to air humidity. The influence of humidity is compensated for by using the signal of a humidity sensor.

15 Claims, 6 Drawing Sheets

(56) References Cited

OTHER PUBLICATIONS

S. Stegmeier, M. Fleischer, A. Tawil, P. Hauptmann, K. Egly, K. Rose, "Mechanism of the interaction of CO2 and humidity with primary amino group systems for room temperature CO2 sensors," Procedia Chemistry 1 (Sep. 2009) 236-239.*

M. Burgmair, M. Simmer, I. Eisele, "Humidity and temperature compensation in work function gas sensor FETs," Sens. Actuators B 93 (2003) 271-275.*

S. Stegmeier et al., "Detection of $CO_2$ with (Hetero-) Polysiloxanes sensing layers by the change of work function at room temperature," Proceedings of the Eurosensors XXIII Conference, Procedia Chemistry 1, pp. 646-649, Sep. 2009.

Hanns-Erik Endres et al., "A capacitive $CO_2$ sensor system with suppression of the humidity interference," Sensors and Actuators B 57 (1999), pp. 83-87.

Japanese Office Action issued Apr. 30, 2013 in corresponding Japanese Patent Application No. 2010-277224.

* cited by examiner

CARBON DIOXIDE SENSOR AND ASSOCIATED METHOD FOR GENERATING A GAS MEASUREMENT VALUE

CROSS REFERENCE TO RELATED APPLICATIONS

This application is based on and hereby claims priority to German Application No. 10 2009 058 072.7 filed on Dec. 14, 2009, the contents of which are hereby incorporated by reference.

BACKGROUND

The invention relates to an apparatus for detecting the carbon dioxide content of air. Furthermore, the invention relates to a method for generating a gas measurement value representing the carbon dioxide concentration in air.

The detection of carbon dioxide is of great interest for a series of applications. Examples include the assessment of air quality in interiors, energy-efficient driving of air-conditioning systems or the monitoring of purified air. The aim of detecting carbon dioxide may be to increase comfort. However, it is also possible to achieve considerable energy savings under certain circumstances.

Thus, in the case of a well-insulated building, for example, almost half of the energy required for air-conditioning can be saved by demand-conforming air-conditioning. In this case, the demand is oriented, inter alia, toward the carbon dioxide content of the air. In the automative sector, too, demand-conforming ventilation and air-conditioning of the interior of the automobile is advantageous. An estimated value for the reduction of consumption for air-conditioning is 0.3 l per 100 km.

Carbon dioxide occurs in a concentration of approximately 380-400 ppm under normal ambient conditions in air. On the basis of this base concentration, a sensor for carbon dioxide has to be able to detect increased concentrations up to 4000 ppm, for example. What is problematic here is that the carbon dioxide molecule is a linear, symmetrical molecule and an electric dipole moment, which can bring about a sensor signal in various transducer principles, is therefore absent. Furthermore, the molecule is chemically very unreactive.

Currently very successful methods for determining the concentration of carbon dioxide can therefore be found primarily in the field of optical spectroscopy. In this case, use is made of the fact that carbon dioxide absorbs light in specific wavelength ranges, for example at a wavelength of approximately 4.3 μm. This enables an accurate and selective measurement of the concentration of carbon dioxide. The chemical reactivity of carbon dioxide is unimportant in this case. What is disadvantageous about optical spectroscopy, however, is the complex construction of the measurement systems and the considerable outlay required for evaluating the measured spectra. This ultimately leads to comparatively large and expensive measurement systems.

Solid-state sensors such as semiconductor gas sensors, for example, avoid the disadvantages of the optical measurement systems. They are small, can be produced by mass production extremely inexpensively in comparison and require less complex signal evaluation. What is disadvantageous about solid-state sensors, however, is that they rely on a certain reactivity of the molecules to be measured and at the same time, however, detect all molecules having indeed a certain reactivity. To put it another way, the solid-state sensors have a low selectivity. This makes it difficult primarily to measure not very reactive species such as carbon dioxide using such sensors, since they usually react very greatly to hydrocarbons or ozone.

The array of potential disturbing gases is extensive in this case. It comprises nitrogen dioxide ($NO_2$), carbon monoxide (CO) and hydrogen ($H_2$), ammonia ($NH_3$), ethanol or hydrochloric acids (HCl), nitrogen monoxide (NO), sulfur oxides ($SO_x$), carbon oxide sulfide (COS), nitrous oxide ($N_2O$) and hydrogen cyanide (HCN), water ($H_2O$) and also organic gases such as methane, ethane, ethene, acetylene and other hydrocarbons such as formaldehyde ($CH_2O$). Further disturbing gases include amines ($NH_2R_1$, $NH_1R_2$, $N_R3$), amides (RC(O)$NH_2$, RC(O)NHR', RC(O)NR'R), acrolein ($C_3H_4O$) and phosgene ($COCl_2$), aromatics such as benzene ($C_6H_6$), ethylbenzene, chlorobenzene, toluene, xylene, styrene and phenol ($C_6H_6O$). Furthermore, there is ozone ($O_3$), the large group of VOCs (volatile organic compounds).

These gases in some instances already occur in normal ambient air, for example ozone. Further sources of gases are fires, cigarette smoke, human activity, the use of chemical agents such as cleaning agents, exposed foodstuffs or technical devices such as printers. Road traffic and even weather conditions also lead to the occurrence of gases.

The document by H.-E. Endres et al., "A capacitive $CO_2$ sensor system with suppression of the humidity interference", Sensors and Actuators B 57 (1999), 83-87, discloses a $CO_2$ sensor based on the principle of a capacitance measurement. In the case of the capacitive sensor disclosed, an additional humidity sensor is used to generate a humidity signal.

A potential-controlled humidity sensor that can be used for this purpose is known from EP 1 176 418 A2, for example. The potential-controlled humidity sensor has a gas-sensitive region which can be polarized independently of humidity. Furthermore, the gas-sensitive region has a relative permittivity that is dependent on the humidity.

What is disadvantageous about the capacitive sensors from the document by H.-E. Endres et al. is that heating of the sensor is necessary. This heating permanently consumes energy. Furthermore, the increased temperature of the sensor relative to room temperature also influences the dynamics of the interactions with surrounding gases, that is to say in other words alters the cross-sensitivities with respect to target and disturbing gases with respect to other sensors that are heated to a lesser or greater extent.

SUMMARY

It is one potential object to specify a gas sensor which enables carbon dioxide to be detected. A further object relates to specifying a method for generating a gas measurement value representing the carbon dioxide concentration in air. Here the intention in each case is, in particular, to compensate for the influence of ambient variables on the measurement signal in a sufficient manner.

The inventors propose an apparatus for detecting the carbon dioxide content of air has at least one gas sensor for outputting a gas measurement value. The gas sensor comprises a gas-sensitive material, for example in the form of a gas-sensitive layer. The gas-sensitive material is configured such that it responds to carbon dioxide. In other words, the gas measurement value changes when there is a change in the concentration of carbon dioxide in the surrounding air. In this case, it is expedient if said change is measurable in the case of a change in concentration of, in particular, 50 ppm $CO_2$, that is to say that the change is greater than the signal noise. In another example, it is also sufficient if the change in the gas measurement value is measurable in the case of a change in concentration of 500 ppm $CO_2$. In the case of the gas sensor, the gas measurement value is generated by an evaluation of the work function of the material.

In this case, mention is made of the concentration of carbon dioxide or water in air. This is also understood to mean that type of measurement of most gas-sensitive materials, in which the absolute presence, i.e. the partial pressure of a gas, is measured rather than a relative proportion of said gas. The gas measurement value is therefore expediently dependent on the partial pressure of carbon dioxide and water.

At least one humidity sensor for outputting a humidity measurement value is furthermore present. Finally, an evaluation device is provided, which is configured for correcting the gas measurement value using the humidity measurement value. In this case, the evaluation device is expediently configured in such a way that the correction has the effect that the influence of a change in the air humidity on the gas measurement value is reduced.

The gas-sensitive material comprises primary amino groups (R—$NH_2$, R=radical, e.g. alkyl radical). Said primary amino groups form, at room temperature in the presence of $CO_2$, reversibly charged species (e.g. bicarbonate and carbamate), which lead to a significant change in the work function. Materials comprising primary amino groups exhibit a significant reversible reaction to changes in the partial pressure of carbon dioxide. At the same time, it has been found that the cross-sensitivities with respect to certain disturbing gases such as, for example, $NO_2$, volatile hydrocarbons or solvents are not high.

In measurements, however, it has emerged surprisingly above all that precisely $CO_2$ sensors based on work function measurement on the material comprising primary amino groups respond, under certain circumstances, to air humidity, to be precise to a greater extent than to the many other disturbing gases. This was unexpected if only because cross-sensitivities do indeed occur in the case of many of the layer materials usually used for the work function measurement, but precisely for water they hardly occur. Examples include the copper phthalocyanines (CuPC), lead phthalocyanines (PbPC) or other phthalocyanines, gallium oxide ($Ga_2O_3$), platinum (Pt) and titanium nitride (TiN).

For disturbing gases that initiate a changed work function in the case of primary amino groups, there would in turn be more clear candidates. This is because air contains in a variable concentration gases which react greatly with primary amines ( . . . —$NH_2$), such as, in particular, nitrogen dioxide ($NO_2$), alcohols (R—OH), nitrogen monoxide (NO), ozone ($O_3$), hydrogen ($H_2$), carbon monoxide (CO), ammonia ($NH_3$), hydrochloric acids (HCl), hydrogen cyanide (HCN), sulfur oxides ($SO_x$), carbon oxide sulfide (COS), nitrous oxide ($N_2O$) and organic gases.

In this case, the influence of water does not prove to be unambiguously clearer than the influence of other sources on the measurement result. The measurement result changes similarly and not immediately differently on account of temperature changes, contamination, and deficiencies in the signal evaluation, zero point drift and hysteresis effects, that is to say biases from previous measurement series. Therefore, the surprisingly ascertained effect of air humidity even remained undiscovered during a series of measurements.

The humidity sensor can be configured for measuring the relative air humidity. It can also be configured for measuring the absolute humidity. This is the case when using optical measurement methods, for example. For the compactness of the construction it is advantageous to use polymer-based humidity sensors, for example. These and other humidity sensors measure a value that is not unambiguously the absolute or relative humidity, and are therefore corrected by a temperature measurement value in order to determine the relative or absolute value. The humidity sensor itself expediently does not react or reacts only insignificantly to carbon dioxide.

The inventors also propose a method for generating a gas measurement value representing the carbon dioxide concentration in air, a gas measurement value is generated by an evaluation of the work function of a material by at least one gas sensor, wherein the gas measurement value is influenced by the presence of carbon dioxide. Furthermore, a humidity measurement value is generated by at least one humidity sensor.

Furthermore, the gas measurement value is corrected using the humidity measurement value in such a way that the influence of the air humidity on the gas measurement value is at least reduced.

It is particularly advantageous if the reaction of the gas measurement value to a change in the relative air humidity by 10% comprises at least 5%, in particular at least 10% or in another example at least 20%, of the intensity of the reaction to a change in concentration of carbon dioxide by 1000 ppm.

A field effect transistor construction is particularly advantageous as the construction for the gas sensor. The basic field effect transistor construction is known from electronic components, that is to say that there are drain and source electrodes and a conducting channel adjacent to a gate electrode. The gas sensor having a field effect transistor construction has the particular feature that the gas-sensitive material is provided adjacent to the conducting channel. As a result, electrical changes in the gas-sensitive material influence the conductivity in the channel.

The functioning of gas sensors on the basis of work function changes or contact potential measurements, such as by a gas-sensitive field effect transistor, for example, is based on the physical fact that adsorbed gas molecules at the material surface either are present as permanent dipoles or induce dipoles. The work function of the material covered with gas then changes by the potential jump at the dipole layer on the surface. This change in potential can be coupled into the gate voltage of a field effect transistor, in which case the change in the threshold voltage with a constant current can then be used as a measurement variable.

Such a field effect transistor construction can be realized by the gas-sensitive material being applied directly to the gate electrode. In this case, it is possible to produce the sensor in large quantities in micromechanical fabrication. In this case, it can be advantageous if the gas-sensitive material is either made very thin or else configured in a gas-permeable fashion, in order to obtain a maximum electrical effect of the gas reactions on the conducting channel.

Particularly advantageously, the GasFET is equipped with an air gap between the sensitive layer and the conducting channel of the field effect transistor construction. The realization of a gas field effect transistor (GasFET), wherein a small air gap (0.5-5 µm) is present between gate electrode and channel region of the transistor, provides for that side of the gate electrode which faces the air gap to be provided, for example coated, with the gas-sensitive material. At the sensitive layer, as a result of the gas-induced change in the electron work function, an additional potential of the order of magnitude of typically 10-100 mV arises, which acts as an additional gate voltage on the transistor.

A particularly advantageous construction provides a GasFET, in particular a hybrid GasFET having a gas-sensitive layer comprising primary amino groups. This is because in this case the read-out of the work function permits operation at room temperature. As a result, not only is energy saved for heating the sensor, but the construction can be simplified from the outside since no heater is required.

It is furthermore advantageous if the gas-sensitive material comprises a polymer. The intensity of the cross-sensitivity with respect to air humidity of polymer-based gas-sensitive layers is dependent on the type of read-out of the signal. Precisely upon transition from known capacitive sensors to read-out by the work function, in particular by a GasFET, altered cross-sensitivities are also afforded alongside the surprising and considerable advantage of measurement at room temperature. Thus, the sensitivity to air humidity is surprisingly high in the case of read-out by the work function such as is performed in the case of GasFETs.

It is particularly advantageous if the evaluation unit is configured for taking account of a temperature signal in the correction of the gas measurement value. In addition, the temperature signal can also be taken into account in any correction of the humidity signal. An influence of the ambient temperature on the measurement can thereby be reduced.

This is particularly advantageous in connection with sensors which are operated at or near room temperature, that is to say for example at temperatures of less than 50° C. In this case, a change in the temperature of the apparatus, that is to say of the sensors, arises generally, but of course in a most pronounced fashion during operation at room temperature, if the ambient temperature changes. In other words, an unheated sensor is subject to the room temperature fluctuations, which brings about changes in the adsorption behavior, chemical equilibrium, inter alia, and, as a result thereof, influences the output signal of the sensor.

Sensors which can be operated at room temperature include, for example, FET-based gas sensors having polymer-based gas-sensitive layers comprising primary amino groups. Therefore, a temperature correction is particularly beneficial for them.

In accordance with one advantageous configuration, the apparatus has a temperature sensor for generating the temperature signal. Temperature sensors can be obtained in a prefabricated and simple fashion. It is likewise readily possible to produce temperature sensors in a micromechanical fashion, for example as a resistance thermometer of thin-film design or as a temperature-sensitive diode or even as a temperature-sensitive FET. By way of example, monolithic integration with the gas sensor and advantageously also with the humidity sensor can thus be achieved, which leads to a particularly small and favorable design. A similar, advantageous possibility is to provide a humidity sensor which itself already generates a temperature signal, and to concomitantly use said temperature signal, that is to say to make it available to the evaluation unit, for example.

However, in an advantageous alternative it is also possible to provide a device for heating the gas sensor and/or the humidity sensor instead of or, if appropriate, in addition to the temperature sensor. By way of example, heating can thus be performed. If this is limited and regulated to 50° C. or 40° C., for example, the sensor is automatically substantially independent of the ambient temperature. At the same time, the heating device can also be configured for concomitantly fulfilling the function for determining the temperature signal. By way of example, a thin- or thick-film heater in the form of a heating meander can be used for this purpose. One possibility in this respect relates to using the heating power required for maintaining the predetermined temperature as a measure of the ambient temperature. If more heating power is required, then the heat dissipation is greater, i.e. either the sensor is exposed to an air flow or colder conditions prevail. In a housing, an air flow is prevented, and so this influence can be ruled out.

Finally, a further alternative to generating the temperature signal relates to exposing the gas sensor and/or the humidity sensor to different temperatures by the heating device. The evaluation device is then expediently configured in such a way that it deduces the ambient temperature from the reactions of gas sensor and/or humidity sensor.

In order to be able to compensate for pressure influences, in a further configuration a pressure sensor is provided. The air pressure can vary for example as a result of altitude above sea level and as a result of weather influences.

It is particularly advantageous if the pressure sensor is realized monolithically with the gas sensor and/or the further sensors present, i.e. produced on a common substrate.

The influence of the air humidity on the gas measurement value can be divided into two effects. The first effect corresponds to the function which the gas-sensitive material could have as humidity sensor. It is totally independent of the presence of carbon dioxide. That is illustrated in FIG. 2. The change from 30% r.h. (relative air humidity) to 0% r.h. constitutes an extreme case, but the changes between 10% r.h. and 60% r.h. that are likewise illustrated in FIG. 2 can occur, under certain circumstances, and in the case of this sensor layer produce a sensor signal which is greater than the useful signal in the case of a change from 400 to 4000 ppm $CO_2$. The two signals are superposed in virtually linear form. In this case, it should be taken into consideration that the sensor responses of the three measurements (FIG. 3 $a,b,c$) are not directly comparable with one another since different sensor layer thicknesses were used for the measurements.

The second effect is that the size of the measurement effect on $CO_2$ is dependent somewhat on the air humidity respectively provided, that is to say that the signal brought about by, for example, a change in concentration of 100 ppm carbon dioxide is dependent on the water partial pressure. Thus, a change in concentration of 100 ppm carbon dioxide in the case of an air humidity of 30%, for example, can produce a change in the electrical signal of 10 mV, while the same change in concentration in the case of 70% air humidity produces a change in the electrical signal of 13 mV. In this case, the difference of 40% air humidity, which itself produces a signal change of 40 mV, for example, is already taken into account and corrected. That is to say that even if the first effect explained further above is completely corrected, the second effect remains and can likewise be corrected in order to increase the accuracy of the carbon dioxide measurement.

In one advantageous configuration, the first effect is corrected. This can be done, for example, on the basis of correction values present in tabular form. It is also possible to carry out the correction analytically using stored coefficients.

It is particularly advantageous for the accuracy of the measurement if the second effect is additionally corrected. In this case, therefore, this not only involves the fact that the excursion of the gas measurement value that is brought about by moisture is discounted, but the remaining gas measurement value, which then originates from carbon dioxide, is additionally corrected on the basis of the humidity. This can likewise be done for example on the basis of correction values present in tabular form. It is also possible to carry out the correction analytically using stored coefficients.

If, in one exemplary embodiment, there is enough memory space in a microprocessor, both effects can also be corrected together, for example by a two-dimensional table of values being stored. The table then supplies, on the basis of the gas measurement value and the humidity measurement value, a value for the concentration of carbon dioxide corrected for both effects.

It is advantageous if the influence of a different response time of the humidity sensor and gas sensor is taken into account. This can be done for example by a procedure in which a check is made to determine whether the temporal change in the gas measurement value and/or in the humidity measurement value exceeds a definable threshold value, and in this case the gas measurement value is taken into account only after a definable waiting time has elapsed. Thus, for example in the case of great signal changes, brought about by the opening of a window or the like, a waiting time of 2 minutes can be complied with, and the further measurement values can be assessed as reliable again only after said waiting time. The measurement values within the waiting time are then expediently discarded.

In this case, it is advantageous if the gas measurement value and/or the humidity measurement value are/is processed in such a way that signal fluctuations which are not brought about by fluctuations of the gas concentrations are not taken into account in the determination of the temporal change. By way of example, the formation of a running average value of the last three, five, or some other number of measurement values can be used for this purpose. Only this moving average value is checked with regard to its temporal change. Further methods for obtaining improved values for the temporal change relate to filtering the measurement values. The filtering can take place in an analog fashion, for example near the sensor by analog electronic components. Filters of, for example, first or second or some other order can be used in this case. The analog filtering advantageously functions passively from the point of view of a microprocessor for the processing of the measurement values, that is to say that the subsequently digitized measurement values are already improved without further complexity in the microprocessor.

However, the filtering can also be effected digitally. For this purpose, the digitized measurement values are processed in the microprocessor, for example, in order to achieve the filtering. A greater flexibility during processing is possible in this case since the measurement values are initially available unchanged.

It is also possible to store the response behavior of the gas-sensitive material in a manner dependent on the humidity level respectively present in the evaluation device. A change that occurs in the gas measurement value is then weighted in a manner dependent on the humidity measurement value. Thus, in the case of low humidities, for example, the change in the gas measurement value is firstly weighted more highly and then, in accordance with the stored time constants for the response of the gas measurement value, the intensified weighting is then correspondingly removed. The response behavior can e.g. be described well in accordance with an exponential function with a humidity-dependent time constant. The gas measurement value is then weighted in an intensified fashion in a time-dependent manner in the case of a change in accordance with the inverse exponential function and then this intensified weighting is then cancelled again according to the time constant singly or multiply. In this case, use is advantageously made of an exponential function whose absolute value falls toward zero, that is to say a function of the form $$K = K_F \cdot e^{-(t-t_0)/T_F}$$

In this case:

K is a correction value for correcting the gas measurement value $K_F$ is a humidity-dependent prefactor $T_F$ is a humidity-dependent time constant $t-t_0$ is the time that has elapsed since the beginning of the correction of the response behavior In this case, K automatically tends toward zero over time. That means that the correction automatically becomes weaker as time elapses. That is expedient since an error in the gas measurement value as a result of the response at differing rapidity likewise becomes smaller over time and completely disappears when a sufficiently long period of time has elapsed.

In a configuration, it is also possible for the evaluation device, for example the microprocessor, to concomitantly take account of the temperature during the correction of the response behavior.

In accordance with one configuration, the apparatus for detecting the carbon dioxide content of air may further comprise a correction unit to reduce an influence on the gas measurement value, from different response times in the humidity sensor and the gas sensor. The correction unit may reduce the influence from different response times by adding a positive or negative correction variable to the gas measurement value, and the absolute value of the correction variable may have an exponentially falling profile.

In accordance with one configuration, the apparatus for detecting the carbon dioxide content of air may further comprise a limit unit to check whether a temporal change in the gas measurement value and/or in the humidity measurement value exceeds a definable threshold value. If the temporal change in the gas measurement value and/or in the humidity measurement value exceeds the definable threshold value, the gas measurement value is taken into account only after a definable waiting time has elapsed.

BRIEF DESCRIPTION OF THE DRAWINGS

These and other objects and advantages of the present invention will become more apparent and more readily appreciated from the following description of the preferred embodiments, taken in conjunction with the accompanying drawings of which.

DETAILED DESCRIPTION OF THE PREFERRED EMBODIMENT

Figure 1:
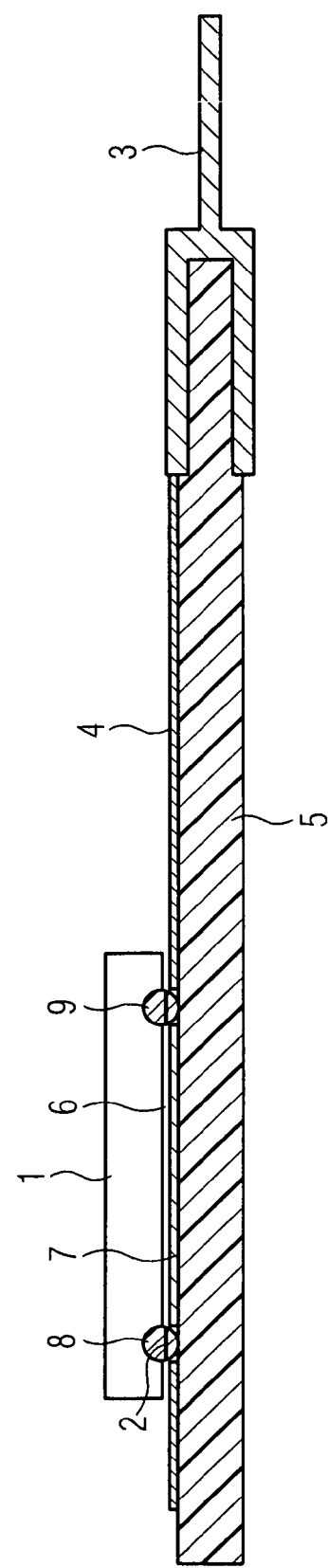
FIG. 1 shows a construction for a carbon dioxide sensor as an SGFET.

Reference will now be made in detail to the preferred embodiments of the present invention, examples of which are illustrated in the accompanying drawings, wherein like reference numerals refer to like elements throughout.

FIG. 1 shows the basic construction of a gas-sensitive FET in accordance with one example of a construction according to the inventors' proposals. The latter comprises a CMOS transistor 1 having a source electrode 8 and a drain electrode 9. In this case, a FET structure in the form of the CMOS transistor 1 is mounted using flip-chip technology onto a ceramic substrate 5 provided with conductor tracks 4. This can be done by a conductive adhesive 2, for example. The gas-sensitive layer 7 is partially applied on the substrate 5 and correspondingly contact-connected to the conductor tracks 4. The gas channel is the air gap 6 between gate and CMOS transistor. The ceramic substrate 5 serves as a carrier of the gas-sensitive layer and simultaneously as a carrier of the entire sensor construction, such that incorporation into a sensor base is not necessary in this example. Plug-in pins 3 can be fitted to said ceramic substrate 5, such that the electronic component can be introduced directly into a single-inline plug connection, for example. Alternatively, other embodiments are also possible, for example the embodiment as an SMD component (surface mounted device).

Figure 2:
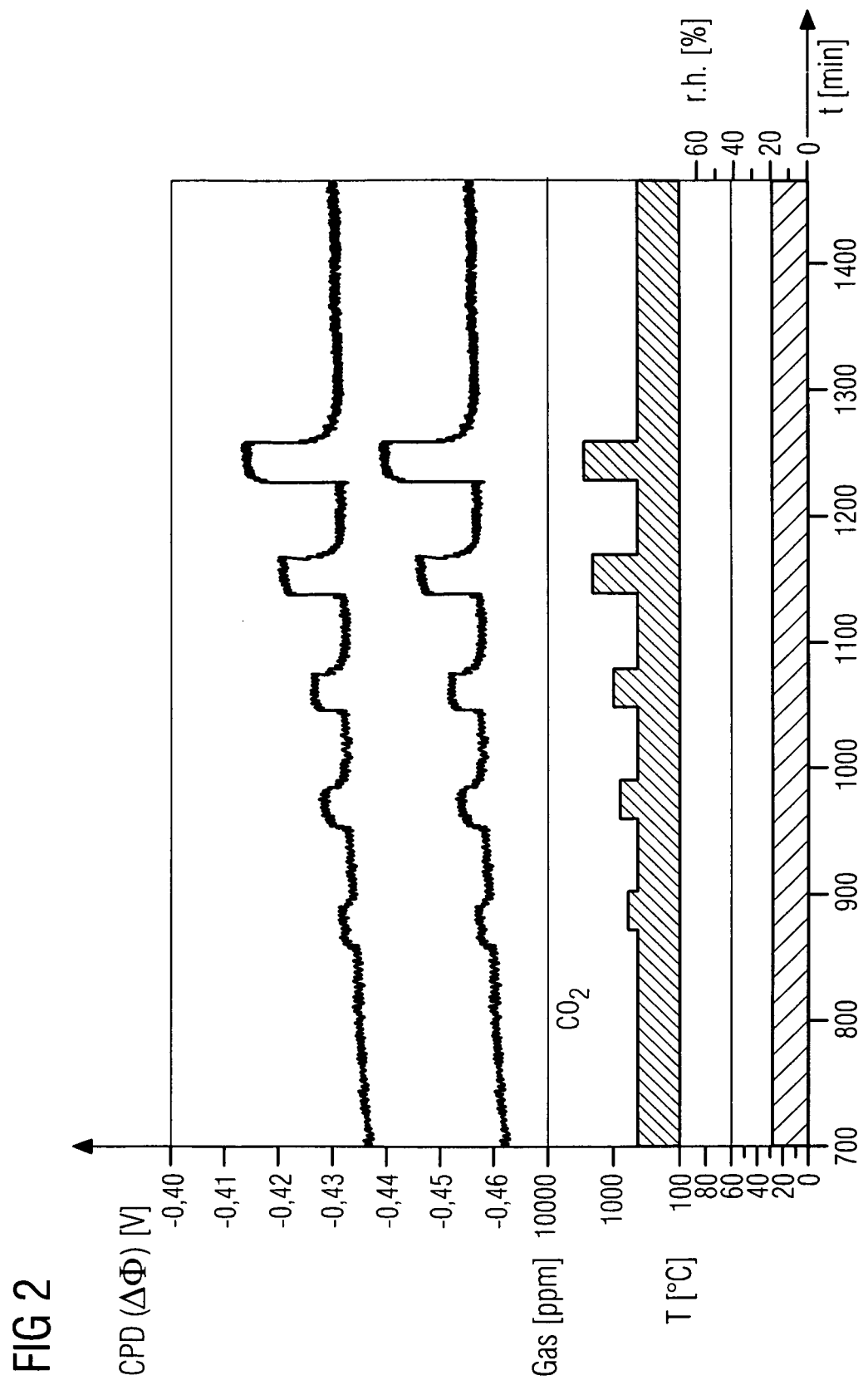
FIG. 2 shows a measurement result of an AMO/PTMS layer for carbon dioxide.

A first sensor, the measurement result of which is illustrated in FIG. 2, has a so-called AMO/PTMS layer as sensor layer. This material system is also designated as heteropolysiloxane, since here the material is formed from two different starting silanes. In order to produce this layer, aminopropyltrimethoxysilane (AMO) and propyltrimethoxysilane (PTMS) are dissolved in methanol. The solution is boiled under reflux for 3 hours in a glass flask with addition of a small amount of water. The resulting solution, after cooling, is applied to a substrate (e.g. gold-coated $Al_2O_3$ ceramic) by a spin-coating process and cured in a furnace in a nitrogen atmosphere at 120° C. for sixteen hours. The layer thus produced has a thickness of 12.8 μm in this example.

FIG. 2 shows two measurement results on the sensor layer thus obtained, by a Kelvin probe. During the measurement duration, the first sensor was operated at room temperature, that is to say without heating. The first sensor has no heating device. The artificially produced gas environment of the sensor layer had a relative humidity of 40%. During the measurement for several hours, the concentration of carbon dioxide was raised from a base level of approximately 400 ppm in intervals in a stepwise manner and reset again to the base level. The smallest increased concentration produced was approximately 600 ppm, that is to say approximately 200 ppm above the base level. In this case, the highest concentration produced was approximately 4000 ppm.

The measurement signal CPD (contact potential difference) exhibits a significant excursion at a concentration of 4000 ppm $CO_2$. In the case of smaller concentration increases, the signal is correspondingly weaker. The signal is clearly discernible even in the case of the smallest concentration increase of approximately 200 ppm.

A second embodiment possibility for the gas-sensitive layer is a cysteamine layer. In order to produce this layer, a cysteamine solution is applied dropwise onto a gold surface of a Kelvin substrate. In order to form thiol-gold bonds, the sample is left to stand at room temperature for two hours.

Afterward, the cysteamine solution is rinsed off with water and the substrate is dried in a nitrogen stream.

A third embodiment possibility for the gas-sensitive layer is a so-called AMO layer as sensor layer. This material system is also designated as polysiloxane, since here the material is formed by polymerization of a siloxane. In order to produce this layer, aminopropyltrimethoxysilane (AMO) is dissolved in methanol. The solution is boiled under reflux for three hours in a glass flask with addition of a small amount of water. The resulting solution, after cooling, is applied to a substrate by a spin-coating process and cured in a furnace in a nitrogen atmosphere at 120° C. for sixteen hours. The layer thus produced has a thickness of 3.9 μm in this example.

Figure 3:
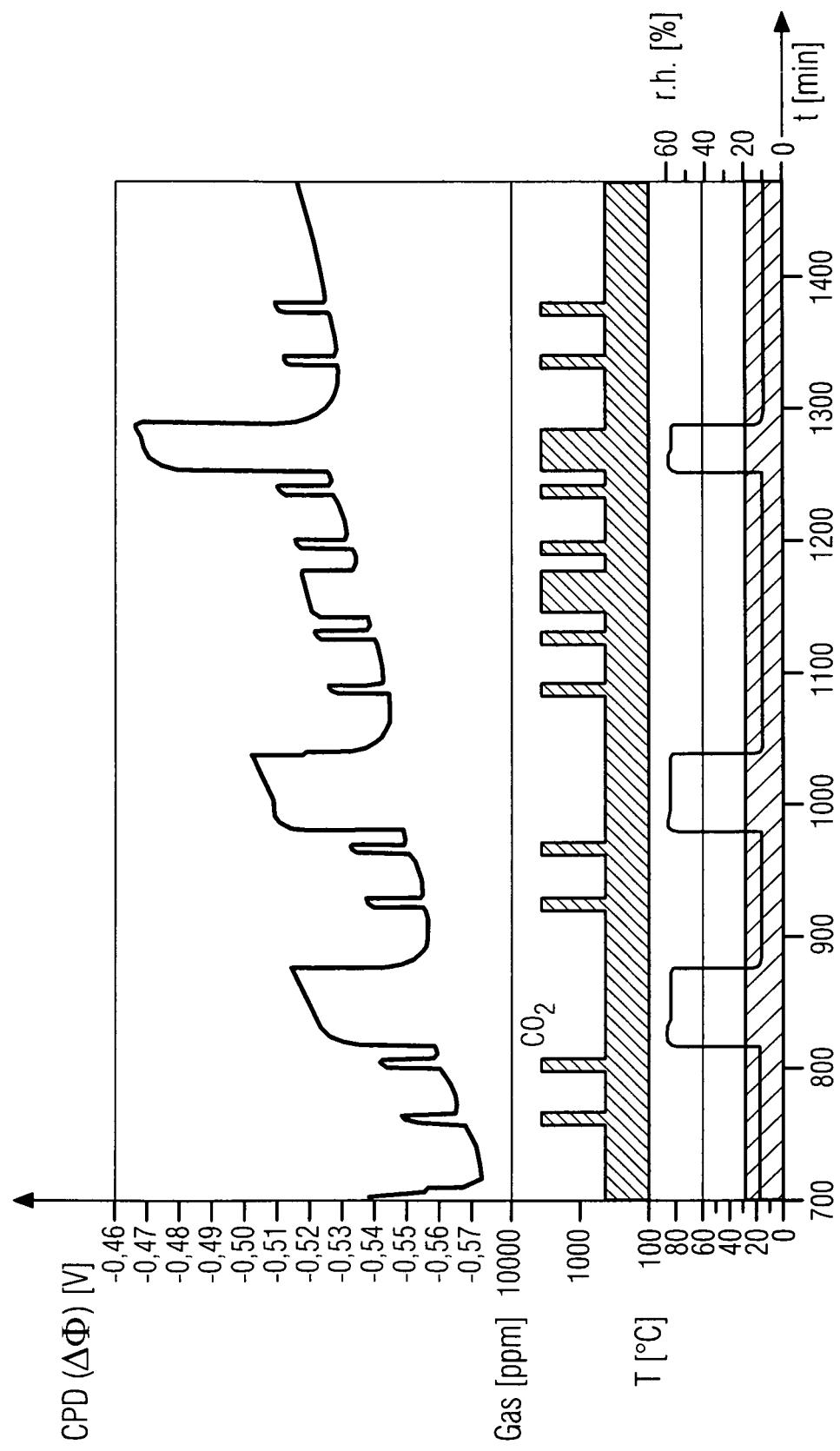
FIG. 3 shows a measurement result of an AMO/PTMS layer for $CO_2$ and water.
Figure 4:
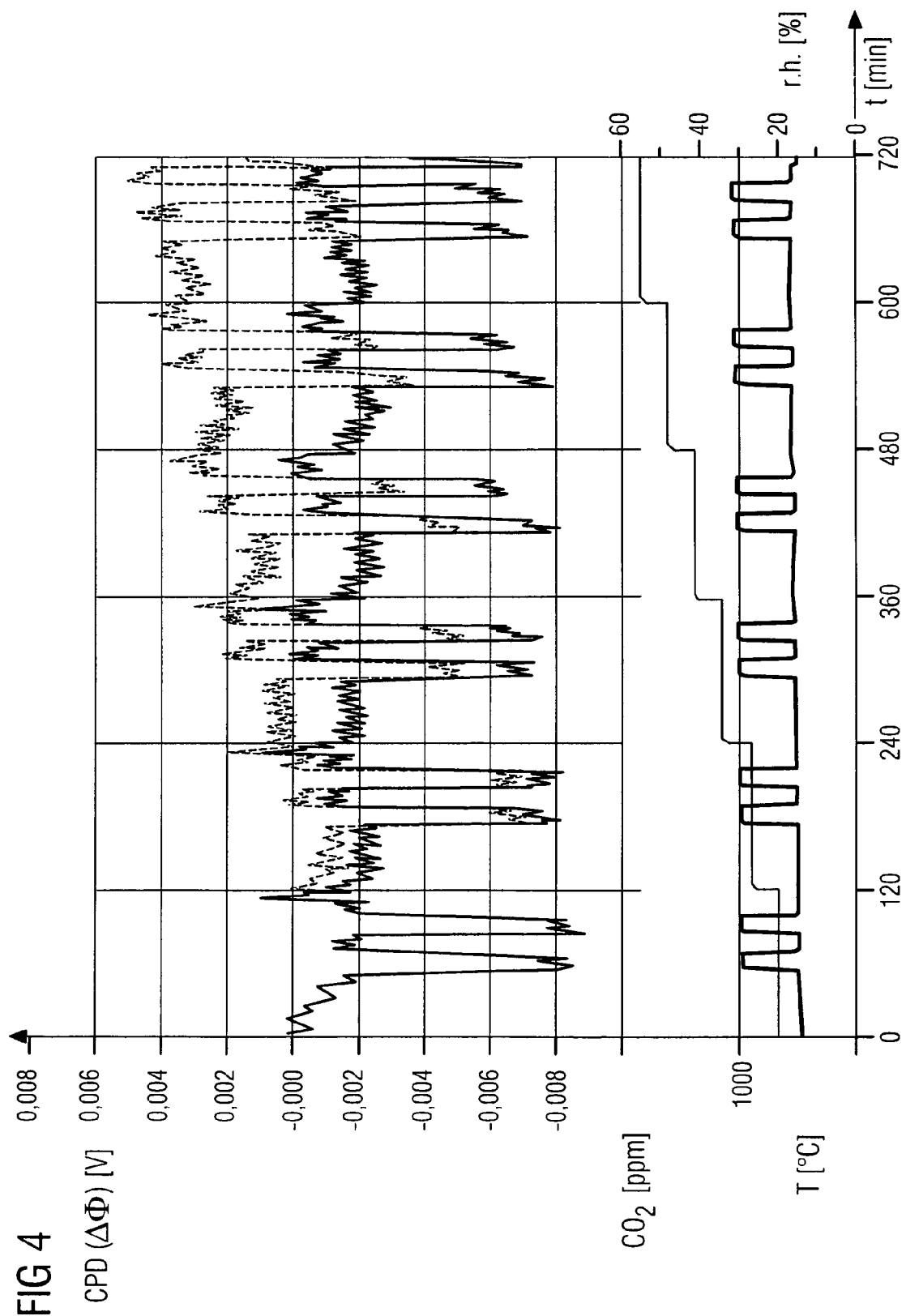
FIG. 4 shows a measurement result of an AMO/PTMS layer with humidity compensation of the base line.
Figure 5:
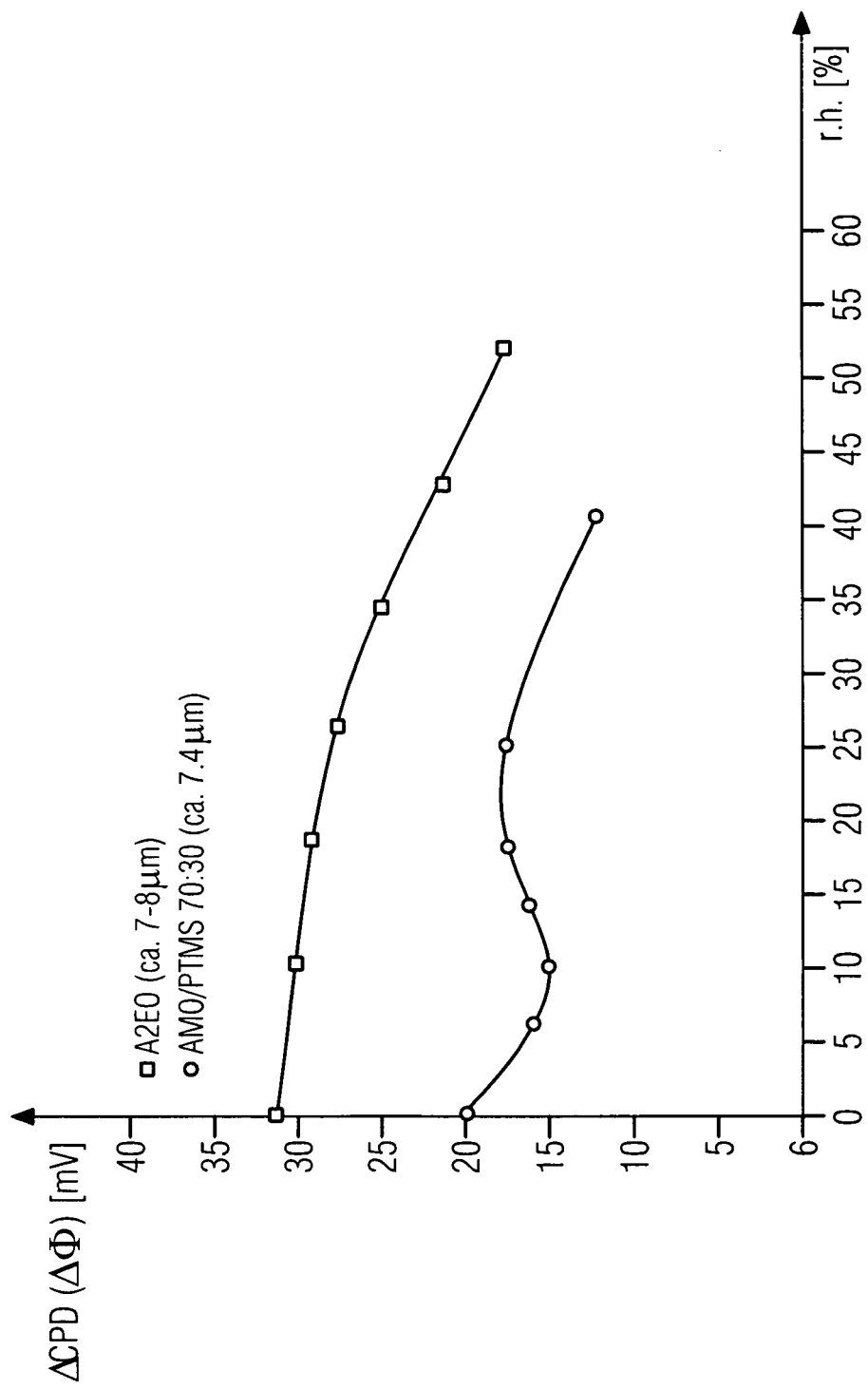
FIG. 5 shows a measurement result of polymer layers for the humidity dependence of the carbon dioxide measurement signal.
Figure 6:
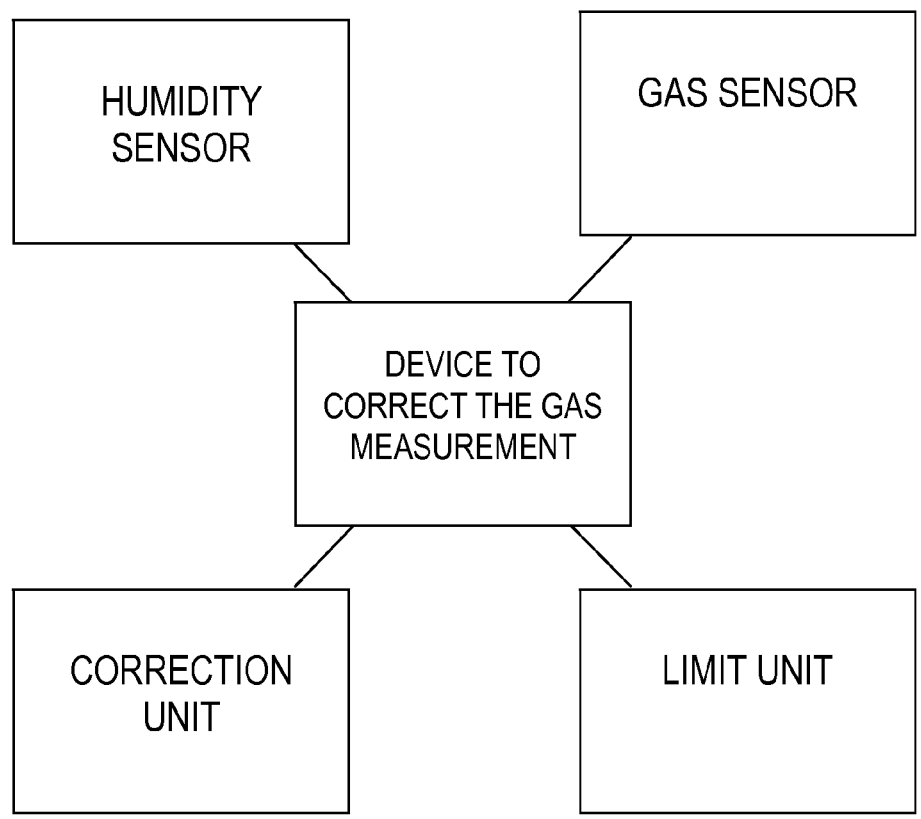
FIG. 6 shows an apparatus to detect a carbon dioxide content in air which comprises a correction unit and a limit unit.

FIG. 3 shows a measurement result on an AMO sensor layer. The construction of the sensor is shown in FIG. 1. During the measurement duration, the sensor was operated at room temperature, that is to say without heating. The artificially produced gas environment of the sensor layer was controlled such that both the humidity and the carbon dioxide concentration were varied. It can be discerned that the sensor layer exhibits distinct reactions to both kinds of changes. The influence of the air humidity is not negligible.

In one exemplary embodiment of a specific sensor construction, the latter has, alongside an FET-based AMO gas sensor, a humidity sensor and a temperature sensor embodied as thin-film metallization. Evaluation electronics, which can either be integrated with the gas measurement chip or be realized outside, records the signals of the humidity sensor, of the temperature sensor and of the gas sensor. The gas measurement value applied by the gas sensor is then corrected by the humidity signal.

This takes place on the basis of characteristic curves for the respective dependencies, said characteristic curves being stored in the electronics. In a first step, a corresponding value is added to or subtracted from the sensor signal. This step generally already corrects the majority of the cross-sensitivity. The influence of the humidity is thereby corrected, in the case of which the currently present carbon dioxide content of the air is unimportant insofar as carbon dioxide signal and humidity signal are thus independent of one another.

In a second step, the change in the sensor signal for determining $CO_2$ is then corrected with a factor in accordance with the stored characteristic curve. In this second step, therefore, the error in the measurement signal that results from the interaction between water and $CO_2$ is corrected.

In a further embodiment, in addition to the correction of the humidity dependence, the temperature dependence of the sensor signal is compensated for with the aid of the temperature sensor. For this purpose, in the first step, firstly the humidity influence and the temperature influence on the sensor base signal are compensated for. Then, once again in accordance with the second step, the sensor excursion is determined and again weighted on the basis of the prevailing humidity and temperature levels in accordance with a stored family of characteristic curves.

This procedure can be employed continuously if identical response kinetics of the two sensors to temperature and humidity change are present. If these are not provided in an ideal manner, the following procedure, for example, is employed. On the basis of the signal of the temperature or humidity sensor it is ascertained that one of the variables has changed significantly (above a certain threshold value which is known to bring about a signal swing that has an influence on the $CO_2$ measurement). As a reaction, for signal outputting there is then a wait until the known response times of the $CO_2$ sensor and/or of the humidity sensor are past and only then is a $CO_2$ signal output again. This ensures that after a rapid humidity change, for example, the $CO_2$ value is again permitted to be trusted.

The invention has been described in detail with particular reference to preferred embodiments thereof and examples, but it will be understood that variations and modifications can be effected within the spirit and scope of the invention covered by the claims which may include the phrase "at least one of A, B and C" as an alternative expression that means one or more of A, B and C may be used, contrary to the holding in *Superguide v. DIRECTV,* 69 USPQ2d 1865 (Fed. Cir. 2004).

The invention claimed is:

1. An apparatus to detect a carbon dioxide content in air, comprising:

at least one gas sensor to output a gas measurement value;

at least one humidity sensor to output a humidity measurement value; and a device to correct the gas measurement value using the humidity measurement value, wherein the gas sensor comprises a gas-sensitive material which responds to carbon dioxide and comprises primary amino groups, the gas sensor is configured to generate the gas measurement value through an evaluation of a work function of the gas sensitive material, the device to correct the gas measurement value is configured to correct for an influence, irrespective of carbon dioxide presence, of air humidity on the gas measurement value, and the device to correct the gas measurement value is configured to correct for an influence of air humidity on a strength of a response of the gas sensor to carbon dioxide.

2. The apparatus as claimed in claim 1, wherein the gas-sensitive material comprises a polymer.

3. The apparatus as claimed in claim 1, further comprising a temperature sensor, wherein the device to correct the gas measurement value is furthermore configured to compensate for a temperature dependence of the gas measurement value, using the temperature sensor.

4. The apparatus as claimed in claim 1, wherein the gas sensor has a field effect transistor with a conducting channel, and an air gap is formed between the gas-sensitive material and the conducting channel of the field effect transistor.

5. The apparatus as claimed in claim 1, further comprising a pressure sensor.

6. The apparatus as claimed in claim 1, wherein the gas-sensitive material is configured such that the gas measurement value reacts to a 10% change in relative air humidity by an amount greater than or equal to 5% of an amount by which the gas measurement value reacts to a 1000 ppm change in concentration of carbon dioxide.

7. The apparatus as claimed in claim 1, further comprising a heating apparatus to heat the gas sensor and/or the humidity sensor.

8. The apparatus as claimed in claim 7, wherein the heating apparatus determines a temperature signal.

9. The apparatus as claimed in claim 8, wherein the temperature signal contains information regarding how the gas measurement value and/or humidity measurement value reacts to different heating levels.

10. The apparatus as claimed in claim 8, wherein the heating apparatus maintains a substantially constant temperature, and the temperature signal is determined based on power consumption required for the heating apparatus to maintain the substantially constant temperature.

11. The apparatus as claimed in claim 1, further comprising a correction unit to reduce an influence on the gas measurement value, from different response times in the humidity sensor and the gas sensor.

12. The apparatus as claimed in claim 11, wherein the correction unit reduces the influence from different response times by adding a positive or negative correction variable to the gas measurement value, and the absolute value of the correction variable has an exponentially falling profile.

13. The apparatus as claimed in claim 1, wherein the apparatus further comprises a limit unit to check whether a temporal change in the gas measurement value and/or in the humidity measurement value exceeds a definable threshold value, and if the temporal change in the gas measurement value and/or in the humidity measurement value exceeds the definable threshold value, the gas measurement value is taken into account only after a definable waiting time has elapsed.

14. The apparatus as claimed in claim 1, wherein the gas-sensitive material responds both to carbon dioxide and to air humidity.

15. A method for generating a gas measurement value representing a carbon dioxide concentration in air, comprising:

generating a gas measurement value by evaluating a work function of a material comprising primary amino groups, the gas measurement value being evaluated using at least one gas sensor, the gas measurement value being influenced by the carbon dioxide concentration;

using a humidity sensor to generate a humidity measurement value; and using the humidity measurement value to correct an influence, irrespective of carbon dioxide presence, of air humidity on the gas measurement value and, using the humidity measurement value to correct for an influence of air humidity on a strength of a strength of a response of the gas sensor to carbon dioxide.

* * * * *